United States Patent [19]
Brown et al.

[11] Patent Number: 5,807,741
[45] Date of Patent: Sep. 15, 1998

[54] NEUTRALIZING MONOCLONAL ANTIBODY AGAINST BOTULINUM NEUROTOXIN SEROTYPE F

[76] Inventors: Douglas Richard Brown, 8917 N. Westland, Gaithersburg, Md. 20877; James Jude Schmidt, 5819 Catoctia Vists, Mount Airy, Md. 21771

[21] Appl. No.: 504,969

[22] Filed: Jul. 20, 1995

[51] Int. Cl.$^6$ .............................. C12N 5/12; A61K 39/395
[52] U.S. Cl. .................. 435/340; 435/70.21; 435/172.2; 530/388.4; 530/387.3; 424/164.1; 424/247.1
[58] Field of Search ............................... 424/150.1, 164.1, 424/163.1, 247.1; 435/69.6, 70.21, 172.27, 240.27, 340; 530/388.4, 389.5, 387.3

[56] References Cited

PUBLICATIONS

Paul, WE. 1993 Fundamental Immunology p.242.

*Primary Examiner*—Lila Feisee
*Assistant Examiner*—Julie E. Reeves
*Attorney, Agent, or Firm*—John F. Moran; Sana A. Pratt

[57] ABSTRACT

Antibodies which neutralize botulinum neurotoxin serotype F are produced using biologically active botulinum neurotoxin instead of toxoid for immunization and exploiting the importance of cross reaction between various serotypes to obtain immune responses, or monoclonal antibodies, to additional serotypes of interest. Methods of preparation and uses of the neutralizing botulinum neurotoxin antibodies are described.

7 Claims, 2 Drawing Sheets

NEUTRALIZING MONOCLONAL ANTIBODY AGAINST BOTULINUM NEUROTOXIN SEROTYPE F

INTRODUCTION

This invention is related to the production and use of novel neutralizing monoclonal antibodies against botulinum neurotoxin serotype F (BNT/F) which are completely protective in vivo against BNT/F, and hybridomas which produce monoclonal antibodies against BNT/F. The invention is directed to the antibodies, to processes of preparing the antibodies, to diagnostic, prophylactic, and therapeutic methods and compositions employing the antibodies, and to investigational, pharmaceutical, and other methods and compositions employing the antibodies.

The sporulating, anaerobic gram-positive bacillus *Clostridia botulinum* produces seven distinct neurotoxins (BNTs) which are among the most potent toxins known. Human botulism poisoning is generally caused by type A, B, E and sometimes, F toxin. Foodborne botulism poisoning is caused by the toxins present in contaminated food, but wound and infant botulism are caused by in vivo growth in closed wounds and the gastrointestinal tract respectively. The toxins primarily act by blocking the neurotransmitter acetylcholine at the neuromuscular junction, causing paralysis. The mechanisms for this blockage are currently under investigation (Schiavo, G. et al. 1992. *Nature* 359: 832–773. All documents cited herein are hereby incorporated by reference thereto).

Each botulinum neurotoxin is first synthesized by the bacteria as a single polypeptide chain with a molecular weight of about 150,000. In most botulinum serotypes, this single chain form is then "nicked" by endogenous protease (s), about one third of the way between the amino- and carboxy-termini, to produce the di-chain form. The latter consists of one light chain (molecular weight about 50,000), and one heavy chain (molecular weight about 100,000), covalently linked by at least one disulfide bond. The light chain contains the original amino-terminal region of the parent single chain form, while the heavy chain has the original carboxy-terminus. (See: DasGupta, B., and Sugiyama, H (1972) *Biochem. Biophys. Res. Comm.* 48: 108–112; Dolly, J. (1992) in Handbook of Experimental Pharmacology (H. Herken and F. Hucho, Eds.), pp 681–717. Springer-Verlag, Berlin.

Until now the only protection against botulism poisoning has been immunization with botulinum toxoid, inactivated toxin(s) which stimulate the production of endogenous antitoxin, but which often produces severe side-effects. There are seven serotypes of BNT, which have little detectable immunological cross reactivity. This has led to the development of the current pentavalent vaccine which is a mixture of five different botulinum toxoids, one each of serotypes A, B, C, D, and E (See: Siegel, L (1988) *J. Clin. Microbiol.* 26, 2352–2356; Anderson, J., and Lewis, G. E. (1981) in Biomedical Aspects of Botulism (G. E. Lewis, Ed.), pp 233–246. Academic Press, Inc., New York). However, there are numerous regions of homology between these seven serotypes, which suggests the potential of producing a protective cross reactive immune response.

Two research groups have identified possible cross reacting monoclonal antibodies (mAbs; Hambleton, P. et al. In *Bacterial Protein Toxins.* ed. J. E. Alouf et al., Academic Press 1984, London. Tsuzuki, K. et al. 1988. *Infect. Immun.* 56: 898–902). These mAbs were obtained by immunization with toxoided BNT, a botulinum neurotoxin that has been rendered non-toxic ("toxoided", chemically inactivated) by incubation with formaldehyde (For example, see: Singh, B., and DasGupta, B. (1989) *Toxicon* 27: 403–410) or with light chains of BNT alone. The mAbs were considered neutralizing or cross reacting or neither. All the antibodies in these publications were assayed in passive neutralization tests, wherein the antibody and toxin are premixed in different ratios, then injected into mice. If no toxicity remains (i.e. no mice die) then the antibody can be considered protective. Based on this criteria, then in the publications referenced, only the anti-tetanus monoclonal antibody afforded protection. This mAb recognizes a conformational epitope which can be lost if the protein is sufficiently perturbed (Arunachalam, B. et al. 1992. *Hybridoma* 11: 165–179). Of 17 mAbs to BNT serotype E (BNT/E) toxoid, all were to heavy chain and 5 were neutralizing. However, light chain is not free from heavy chain in nature, and a role for non-native epitopes in the immune response cannot be discounted.

We note that BNT/A is used in human therapy for several neurological conditions (Anderson, T. J. et al. 1992. *J. Royal Soc. Med.* 85: 524–529. Newman, N. J. and Labert, S. R. 1992. *Neurology* 42: 1391–1393. Zwimer, P. et al. 1992. *Laryngoscope* 102: 400–406. Burgunder, J. -M. 1992. *Schweiz Med. Wochenschr* 122: 1311–1316). Low doses of BNT/A are administered repeatedly and physicians have found that some patients lose responsiveness to the therapy. Neutralizing antibody responses have been found in some of these patients (Hambleton, P. et al. 1992. *Brit. Med. J.* 304: 959–960), suggesting that it is possible to produce mAbs to native BNT.

There are no monoclonal antibodies currently available which neutralize any or all serotype of botulinum neutotoxin based on the requirement that an antibody afford protection against a toxin without the necessity of premixing the two. That is, the toxin and antibody could be administered to an animal by different routes and/or at different times, and the animal would survive. Those which claim neutralization in print, instead provide delayed times to death (Shone, C. et al. 1985. *Applied and Environmental Microbiology* 50:63–67; Kozake, S. et al. 1987. *Infec. Immun.* 55: 3051–3056; Noah, C. W. et al. 1995. *J. AOAC International* 78: 381–385). Therefor, there is a need for a monoclonal antibody which can neutralize the toxin and provide protection against the different serotypes of BNT.

In addition, a new vaccine leading to improved titers and/or a long term immunity is of value. Unfortunately, there is no direct experimental evidence to provide guidance regarding immunogen selection for this new BNT vaccine. A neutralizing monoclonal antibody can provide guidance as to epitopes useful in vaccine development for cross protection.

SUMMARY

The subject invention relates to a monoclonal antibody, referred to as 7F8G2.H3, and to the uses thereof.

The production of monoclonal antibodies in general was first described by Kohler and Milstein (*Nature* 256: 495, 1975) where monoclonal antibodies directed to sheep red blood cells were prepared by fusing a specific antibody-producing B lymphocyte with a tumor cell, resulting in an "immortal" self-reproducing hybrid clone (or "hybridoma") than can synthesize, in a test tube (in vitro) or an animal (in vivo), a single, monoclonal antibody. Such a hybridoma, is in effect, a self-reproducing cell "factory" which can produce a potentially limitless supply of an antibody with single, predefined specificity.

We undertook to prepare novel self-producing cell lines which synthesized monoclonal antibodies directed toward BNT. All previous investigations have taken the approach of immunizing an animal with a toxoid and searching for an antibody response to the toxoid which will cross react with the toxin and which will be protective. Priming the immune response with irrelevant epitopes will predispose the immune response to those epitopes, even in the event the animal is later boosted with native toxin. We believe it is necessary to avoid priming the immune system to toxoided epitopes of the botulinum neurotoxin. We avoided misdirected immune responses by immunizing with increasing sub-lethal doses of the native toxins. This is the first instance of immunizing against botulinum toxin using only active botulinum toxin as an immunogen. Furthermore, we began with botulinum neurotoxin serotype E, which can be purified in a single chain form (BNT/Esc) which is 100 fold less toxic than the nicked form. This allowed us to begin with higher doses than would have been possible with other serotypes. To produce a monoclonal antibody against serotype F, we employed reported cross reactivity between serotypes E and F. Mice, previously immunized against BNT/E could tolerate higher doses of BNT/F compared to naive mice. This led to the isolation of the monoclonal antibody 7F8.G2.H3 which is capable of providing in vivo protection when injected intravenously followed one hour later by an intraperitoneal injection of the toxin.

Accordingly, it is one object of the present invention to provide self-producing carrier cells, capable of producing a neutralizing monoclonal antibody against BNT/F.

It is a further object to provide the antibodies so produced.

A still further object is to provide an in vitro process for producing the antibodies.

An even further object is to provide an in vivo process for mass-producing the antibodies from the carrier cells.

Another object is to provide methods and compositions for using the antibodies in the diagnosis, prophylaxis, and treatment of disease caused by *Clostridium botulinum*.

Still another object is to provide compositions containing the antibodies useful for immunological or biochemical analyses of *Clostridium botulinum*.

An even further object is to provide compositions containing the antibodies suitable for isolating or purifying toxins from mixtures containing toxins and other substances.

Another object is to provide compositions containing the antibodies useful for the neutralization and/or removal of BNT from other material and solutions.

Yet another object of the present invention is to provide an antigenic neutralizing epitope by mapping the antigenic determinant recognized by the monoclonal antibody of the present invention, said antigenic determinant being common to all the botulinum neurotoxin serotypes. Such an epitope would be useful for designing a vaccine protective against all the seven serotypes of botulinum.

Other objects and advantages of the present invention will be set forth in part in the description which follows, and in part will be obvious from the description or may be learned by practice of the invention.

DETAILED DESCRIPTION

Figure 1:
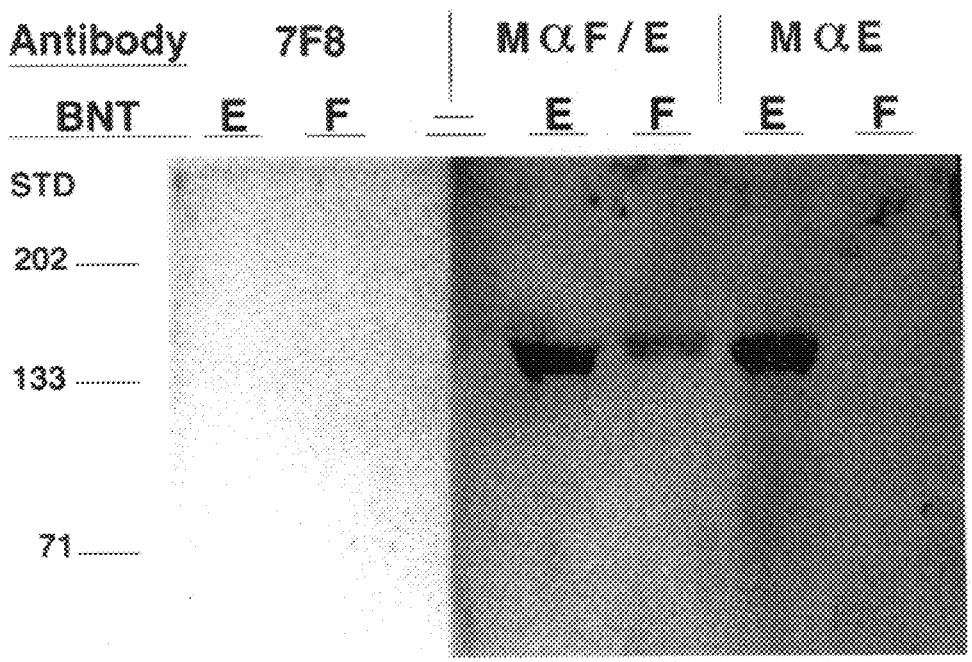
FIG. 1 shows a Western blot of mAb 7F8.G2.H3 against botulinum neurotoxins E and F.

The present invention provides monoclonal antibodies which neutralize BNT/F. The antibodies are produced by hybridoma, F197/7F8.G2.H3 deposited on May 2, 1996 at the American Type Culture Collection, Rockville, Md. 20854, USA, an International Depository Authority, with the ATCC designation HB-12102.

Also provided by this invention is a process for producing such antibodies, said process encompassing culturing said hybridomas in vitro or in vivo. A hybridoma is characterized by the ability to produce a homogeneous antibody (monoclonal antibody) specific to a certain antigenic determinant and also is capable of growing and reproducing in vitro.

The preparation and characterization of hybridomas and resulting antibodies reactive with BNT/F as well as various methods and compositions employing the antibodies, will be better understood by reference to the following description, which sets forth the preferred embodiments of the invention.

As indicated, the scope of the present invention embraces any hybridomas, including, but not limited to, F197/7F8.G2.H3 ATCC designation HB-12102 which produces monoclonal antibody 7F8.G2.H3 and reacts with BNT/F. This specification describes in detail the steps taken by the inventors to produce the above cell line.

Generally, hybridomas are obtained by the following process. Firstly, spleen cells (splenocytes: hereinafter sometimes referred to as S cells) from a mammal such as a mouse or rat are fused with myeloma cells which are deficient in hypoxanthine-guanine phosphoribosyl transferase (hereinafter sometimes referred to as M cells), in the presence of a fusion mediator such as polyethylene glycol (PEG). The fused cells are cultivated using a multiwell plate in a medium containing hypoxantine-aminopterin-thymidine (HAT) in order to effect the selective growth of S-M hybrids while preventing the growth of the other cells including M-M hybrids and the remaining M cells which did not participate in the cell fusion. Hybridoma cells secreting the desired antibody are then cloned by an appropriate method such as the limiting dilution method from the wells in which the cells propagated. The hybridoma thus cloned can be cultivated in vitro or in vivo, e.g., in a mouse abdominal cavity, in order to have it produce the monoclonal antibody in large amount.

The antibody of the present invention is produced by the cultivation of a hybridoma which is obtained by the cell fusion of two type of cells, one being antibody producing cells of a mammal, e.g., a mouse, which has been immunized with biologically active botulinum neurtotoxin. The mammal may be selected from such animals as mice, rats, rabbits, guinea pigs, etc. which are normally employed for raising antibodies. For example, a mouse can be immunized intraperitoneally or subcutaneously with BNT/Esc. The administration should be repeated several times at intervals of 2 to 3 weeks with an initial dose of 1 ng or less, increasing by factors of 5 to 10 for succeeding doses, in 50 $\mu$l of adjuvant, until an antibody response can be detected by ELISA or 1 microgram of antigen (toxin) can be administered. Following a course of immunizations with BNT/Esc, mice can be successfully immunized with nanogram doses of other, active, cross reactive, BNTs, such as BNT/F. In the three days prior to excision of the spleen, the antigen (toxin) is administered in microgram amounts both intravenously and intraperitoneally. Spleen cells are then obtained and used for the production of hybridoma cells lines.

Since cross reactivity between BNT/Esc and BNT/F has been detected by a native blotting technique, which was not readily detected by ELISA, a similar analysis can be utilized in order to detect cross reactions between BNT/Esc and other serotypes. In addition, monoclonal antibodies specific for other serotypes of BNT can be prepared by, for example, procuring the single chain form of other serotypes of BNT, immunizing mice with this less toxic variant of BNT, isolating monoclonal antibodies specific for the administered BNT sertotype, and then finding cross reactions between the said serotype and other BNT serotypes. For example, the single chain, less toxic form of BNT/B (BNT/Bsc) can be used for immunizing mice and the resulting monoclonal antibodies against BNT/B used to find cross reactions between BNT/B and other serotypes.

When carrier cells are employed in the invention, they are principally characterized by being self-reproducible, and by having genes that code for the production of monoclonal antibodies which neutralize BNT/F. These carrier cells can be cells lines such as human-nonhuman (Nowinski et al., Science, 210:537, 1980) or wholly nonhuman hybridomas (Kohler and Milstein, 1975, supra) or transformed parental lymphoid cells (Steinitz et al., Nature 269:420, 1977). Each of the above four publication is hereby incorporated by reference. These references, in combination with the following Examples, would enable a person skilled in the art to prepare carrier cells of a human or nonhuman animal species capable of producing monoclonal antibodies reactive with BNT/F. For example, spleen cells or peripheral blood lymphocytes obtained from human donors immunized with or previously exposed to toxins can be fused with a mouse myeloma fusion partner, yielding a self-reproducing human-mouse hybridoma which produces human monoclonal antibody reactive with BNT/F.

Another approach to the preparation of self-reproducing carrier cells that secrete human or nonhuman monoclonal antibodies reactive with botulinum toxin involves virus transformation of the appropriate B lymphocyte clone. Steinitz et al. (1977, supra) employed such a procedure to prepare specific human antibody to the synthetic hapten NNP(4hydroxy-3,5dinitrophacetic acid). According to this technique, for example, peripheral blood lymphocytes from human donors immunized with the toxin or previously exposed to the toxin can be isolated on Ficoll-Hypaque. A B lymphocyte population enriched in respect to the production of antibodies reactive with the toxin is prepared and infected with Epstein-Barr Virus (EBV). The EBV-infected B lymphocytes are transformed into continuously proliferating cell lines ("immortal"), and those secreting antibodies reactive with the toxin are identified by ELISA or other appropriate assay and cloned, essentially as described for hybridomas previously.

The procedures outlined above for obtaining human or nonhuman monoclonal antibodies reactive with botulinum toxin employing B lymphocytes fused with tumor cells (hybridomas) and virus-transformed B lymphocytes are similar in all respects except the method by which "immortalization" of the appropriate B lymphocyte clone is achieved. Both techniques entail preparation of biologically active botulinum neurotoxin, immunizing with ever increasing sub-lethal dosed of native toxins, immunizing with a more lethal dose of a cross-reacting active toxin, selecting and cloning of self-reproducing carrier cells producing monoclonal antibodies reactive with the toxin, growth of these cells in continuous culture, and recovery of the monoclonal antibodies produced.

Just as a variety of different systems and methods might be employed to select for and reproduce genes specifying the production of monoclonal antibodies reactive with botulinum neurotoxin, so might a variety of antibodies result from these measures that are distinct from the specific antibody illustrated in the Examples below yet still clearly within the definition of the invention. Once again, the salient feature of such antibodies, for the purposes of this invention, besides their monoclonality, is their ability to neutralize BNT/F in vitro and in vivo. Thus, the invention includes any monoclonal antibody that neutralizes BNT/F, regardless of species of origin, isotype, molecular specificity, affinity, method of production (whether in vitro or in vivo), or type of carrier cell employed in its production.

The monoclonal antibody of this invention is a reagent that may be used to identify BNT/F, or microorganisms bearing BNT/F, in the tissues or body fluids of patients (or animals) infected with these microorganisms, thus permitting rapid and accurate immunological diagnosis of such infections. This form of diagnosis is made possible, in part, by the great specificity of the monoclonal antibody of this invention compared with conventional, polyclonal antibodies reactive with BNT/F.

The monoclonal antibody of this invention is also useful for the immunological detection of BNT/F or BNT/F-bearing organisms present as contaminants in water, biologicals, pharmaceuticals or other materials. Detection is rapid, sensitive, and highly specific.

A diagnostic composition in accordance with the present invention contains a concentration of the antibody effective to diagnose an infection, detect toxin, or demonstrate toxin bearing microorganisms. The antibody can be packaged and sold in freeze-dried or other acceptable form for diagnostic use. It may be mixed with a suitable carrier, attached to an appropriate solid phase (e.g., latex particle, or plastic microtiter plate), conjugated with an enzyme or dye, or radiolabeled, depending on what immunological method is employed.

In a diagnostic or detection method in accordance with this invention, the antibodies of the present invention may be mixed with a sample of body fluid or blood or tissue removed from a person (or animal) suspected of being infected with a BNT/F bearing microorganism, or sample of water, biological, pharmaceutical or other material contaminated with endotoxin or an endotoxin-bearing microorganism, and the degree of reaction in the resulting mixture measured. The amount of antibody required to carry out the diagnosis or accomoplish the detection depends upon factors that include the amount of sample to be tested, the amount of toxin or number of microorganisms present, an the type of assay used. The monoclonal antibody of the present invention can be employed in any diagnostic or detection assay system, of which immuno-fluorescence assays, radioimmunoassays, and enzyme-linked immunosobent assays are examples. Further, the monoclonal antibody of the present invention can be used in a competitive binding or inhibition assay to measure other antibodies, either monoclonal or polyclonal, reactive with BNT/F.

The monoclonal antibody of this invention is a reagent that may be used for the immunoprophylaxis or therapy of Clostridia botulinum infections, or their consequences. These clinical applications of the monoclonal antibody of the invention are supported by its specificity for BNT/F, its ability to neutralize the biological activity of BNT/F, and its producability in virutally limitless supply.

A composition according to the present invention contains a concentration of the antibody effective in preventing or treating (i.e. ameliorating) infections caused by BNT/F-bearing microorganisms, or the consequences of such infections. The antibodies can be packaged and sold in freeze-dried or other acceptable form, and/or mixed with a therapeutically acceptable carrier, such as a balanced aqueous salt solution.

An immunoprophylactic or therapeutic method in accordance with this invention entails the administration of the monoclonal antibody of the invention by injection or infusion prior to (prophylaxis) or following (therapy) the onset of an infection caused by a BNT/F-bearing microorganism. The amount of antibody required to prevent or treat such an infection or its consequences depends upon such factors as the type and severity of the infection, the size and weight of the infected patient, and the effectiveness of other concomitantly employed modes of prophylaxis or therapy.

The monoclonal antibody of the present invention is useful as a reagent for research related to the structure and function of botulinum neurotoxins. The exquisite specificity as well as its ability to neutralize BNT/F allows it to be used for immunochemical and structure-activity analyses of *Clostridia botulinum* neurotoxins. Mapping of the antigenic epitope recognized by the monoclonal antibody of the present invention will lead to the identification of similar epitopes present on other serotypes of botulinum, and the development of a vaccine protective against all the seven serotypes of botulinum neurotoxin.

Mapping of the antigenic epitope can be accomplished by several methods known to people in the art, one of which is described for an example. Monoclonal antibody (mAb) 7F8.G2.H3 detects native BNT/F by ELISA and on native blots. Either technique can be employed to define the epitope. The first step is to determine which chain, light or heavy, mAb 7F8.G2.H3 binds to. These chains can be separated gently on a reducing native polyacrylamide gel. The separated chains can be blotted to nitrocellulose and probed with mAb 7F8.G2.H3. The following comments assume binding to the heavy chain, as its analysis will be more involved. However, should it bind to the light chain the analysis would proceed in an analogous fashion. The heavy chain can be further sub divided by enzymatic cleavage or though employment of molecular biological techniques. Repeated blots of smaller and smaller fragments will eventually result in fragments of BNT/F which are not bound by mAb 7F8.G2.H3. Conformation of the BNT/F may be essential to binding. As one identifies a fragment of BNT/F which does not bind while a similar but somewhat larger one does, the possibility of loss of conformation of the BNT/F fragment must be considered. Eventually, a minimal fragment required for recognition by mAb 7F8.G2.H3 will be generated. At this point, synthetic polypeptides can be produced and used to compete with the minimal fragment for binding with the mAb 7F8.G2.H3. In this way, discontinuous epitopes can be defined.

Described below are examples of the present invention which are provided only for illustrative purposes, and not to limit the scope of the present invention. In light of the present disclosure, numerous embodiments and uses of the invention within the scope of the claims will be apparent to those skilled in the art.

EXAMPLES

Initial Immunization with Botulinum Neurotoxin, Serotype E

The dose of botulinum neurotoxin, serotype E, single chain form (BNT/Esc) which is lethal to 50% of the mice (mLD50) when injected by intraperitoneal (IP) route was determined. This dose would become the immunizing dose received by the initial group of mice.

Mice were anesthetized prior to the intrasplenic injections with 0.05 to 0.07 ml of the following mixture: 1.5 ml Ketamine (100 mg/ml), 1.5 ml Xylazine (20 mg/ml), 0.5 ml Acepromazine (10 mg/ml). A small incision was made on the left side of each mouse to reveal the spleen. The spleen was injected with the previously determined dose (1 IP mLD50) of BNT/Esc in a 50 µl volume in Ribi adjuvant. The peritoneum was closed with adsorbable suture material and the skin was closed with surgical staples, which were later removed. Surgery was performed on approximately thirty mice per day. It was noted that 1 IP mLD50 dose was not equivalent to 1 mLD50 dose given by an intrasplenic (IS) route. The administered dose was increased over the next two days of surgery until the IS mLD50 was apparently exceeded, where upon the dose was reduced.

| Immunization/Challenge with BNT/Esc | | | |
|---|---|---|---|
| Group | Day | Dose | Survivors/Total |
| I | 0 | 1.1 ng | 31/32 |
| II | 2 | 1.5 ng | 23/31 |
| III | 6 | 3.0 ng | 12/29 |
| IV | 8 | 2.0 ng | 24/29 |

Surviving mice received increasing doses of BNT/Esc, in Ribi adjuvant, via subcutaneous route approximately every two weeks. Final booster immunizations were of 1.4 µg of BNT/Esc.

Immunization of BNT/Esc Immunized Mice with Botulinum Neurotoxin, Serotype F(BNT/F)

Six month old mice from the above BNT/Esc immunization were immunized with BNT/F. Mice received increasing doses of BNT/F SC, in a 50 µl of Ribi adjuvant on the days indicated below.

| Immuno-challenge with BNT/F | | | |
|---|---|---|---|
| Day | ng | IP mLD50 | Survivors/Total |
| 0 | 1 | 18 | 3/8 |
| 15 | 1 | 20 | 3/3 |
| 49 | 6 | 105 | 3/3 |
| 59 | 28 | 500 | 3/3 |
| 70 | 170 | 3,050 | 3/3 |
| 117 | 1,000 | 18,000 | 3/3 |
| 118 | 2,000 | 36,000 | 3/3 |
| 119 | 5,000 | 90,000 | 3/3 |

Discovery of 7F8

The mice were sent to a contractor for construction of hybridomas (fusion F197). Hybridoma culture supernates were returned for assay by enzyme-linked immunosorbant assay (ELISA). Original screening was by sandwich ELISA. Horse anti-BNT/F (100 µl) was applied to polystyrene plates at a 1:1000 dilution, at room temperature for one hour. Excess horse anti-BNT/F was washed off and the plates were blocked with 275 µl per well of 5% bovine serum albumin (BSA). Blocking was accomplished overnight at 4° C. BNT/F was added to each well at 2ng per well in a 100 µl volume. This was incubated for one hour at room temperature. Excess BNT/F was washed off and the plates were incubated with 100 µl of hybridoma culture supernates per well for one hour at room temperature. Hybridoma culture supernates were washed off and 100 µl of goat anti-mouse-Ig(GAM) conjugated to horse radish peroxidase (HRP) was applied to each well at a 1:400 dilution. The rest of the reagents were standard to the K&P ELISA kit. Results from one of the plates (plate 7) is shown below.

|   | 1 | 2 | 3 | 4 | 5 | 6 | 7 | 8 | 9 | 10 | 11 | 12 |
|---|---|---|---|---|---|---|---|---|---|---|---|---|
| A | −0.128 | +0.147 | −0.097 | −0.085 | +0.084 | −0.071 | +0.208 | −0.109 | −0.133 | −0.105 | +0.018 | P0.000 |
| B | +0.110 | −0.091 | −0.049 | +0.006 | −0.110 | −0.053 | +0.198 | −0.019 | +0.293 | −0.081 | +0.446 | +0.643 |
| C | −0.102 | −0.034 | −0.056 | +0.440 | −0.066 | +0.006 | +0.284 | −0.064 | +0.232 | −0.036 | +0.414 | −0.676 |
| D | +0.073 | −0.028 | −0.071 | +0.245 | −0.012 | −0.086 | +0.189 | −0.031 | −0.056 | −0.073 | +0.292 | |
| E | +0.010 | −0.062 | +0.154 | −0.067 | −0.006 | +0.030 | −0.076 | +0.006 | −0.084 | −0.023 | +0.400 | |
| F | −0.047 | −0.040 | −0.069 | +0.263 | +0.038 | −0.037 | +0.046 | +0.519 | +0.001 | +0.044 | +0.064 | |
| G | −0.027 | +0.087 | +0.020 | +0.087 | +0.048 | +0.319 | +0.009 | +0.399 | +0.169 | +0.053 | +0.018 | |
| H | −0.083 | +0.012 | −0.008 | +0.125 | +0.119 | +0.163 | +0.126 | +0.111 | +0.331 | +0.010 | +0.136 | |

The cell line from plate 7, row F, column 8 (F197/7F8), in addition to eight others, was selected for further study.

Preliminary tube neutralization data (not shown) indicated clone F197/7F8 was of interest. Limiting dilution was performed twice in order to clone this cell line. Production of the monoclonal 7F8 was monitored by indirect ELISA. Conditions were similar to that described above for the sandwich ELISA, with the following exceptions. Polystyrene plates were coated directly with 200 ng of BNT/F per well. 5% skim milk was used as the blocking agent. The secondary antibody, goat anti-mouse(GAM)-HRP was used at a 1:5000 dilution.

All subclones produced monoclonal antibodies with essentially the same ELISA data (not shown). Cell line F197/7F8.G2.H3 ATCC designation HB-12102, which produces monoclonal antibody (mAb) 7F8.G2.H3, was selected for further study.

Test Tube Neutralization Assay

Preparation of diluted BNT/F. The stock solution of BNT/F, from WFRI, (Wisconsin Food Research Instituted, University of Wisconsin) contained $1.8 \times 10^7$ mLD50 per mg (1 mg/ml). We prepared 50 IP mLD50/ml in PBS. Each mouse would receive 280 picograms.

Positive and negative picontrols were conducted by administration of 1:100 dilutions of mouse anti-BNT/F (MaF/E) or normal mouse sera (NMS) were prepared in PBS.

Preparation of 7F8.G2.H3. Serial 10 fold dilutions of mAb 7F8.G2.H3 were made.

Neutralization of BNT/F. Diluted BNT/F (0.5 ml) was mixed with 2.0 ml of hybridoma culture supernate from or the control serum dilutions. These were incubated at 25° C. for 1 hour.

Bioassay. Half a ml was injected ip into four mice per preparation. Results are expressed as survivors/total.

Stoichiometry of 7F8.G2.H3 against BNT/F. Ten fold dilutions.

| Dilution Factor | Day 7F8/Tube | 1 S/T | 2 S/T | 4 S/T | 9 S/T | 19 S/T |
|---|---|---|---|---|---|---|
| $10^{-1}$ | 1.12 mg | 4/4 | 4/4 | 4/4 | 4/4 | 4/4 |
| $10^{-2}$ | 112 ug | 4/4 | 4/4 | 4/4 | 4/4 | 4/4 |
| $10^{-3}$ | 11.2 ug | 4/4 | 4/4 | 4/4 | 4/4 | 4/4 |
| $10^{-4}$ | 1.12 ug | 4/4 | 2/4 | 2/4 | 2/4 | 2/4 |
| $10^{-5}$ | 112 ng | 4/4 | 0/4 | | | |
| $10^{-6}$ | 11.2 ng | 2/4 | 1/4 | 1/4 | 1/4 | 1/4 |
| $10^{-7}$ | 1.12 ng | 1/4 | 0/4 | | | |
| $10^{-8}$ | 112 pg | 0/4 | | | | |
| 1:200 MaF/E | | 4/4 | 4/4 | 4/4 | 4/4 | 4/4 |
| 1:200 NMS | | 0/4 | | | | |

The neutralization experiment were repeated to further define the neutralizing capability of this mAb.

Dilutions of 7F8.G2.H3 from $10^{-2.7}$ to $10^{-4.2}$ were tested for protection from BNT/F and more concentrated 7F8.G2.H3 for protection from BNT/$E_{SC}$. Dilutions of 7F8.G2.H3: To make the initial $10^{-0.3}$ dilution, 1.250 ml of the original ascites were added into 1.25 ml PBS.

To make the secondary 5 fold dilutions of $10^{-1}$ and $10^{-1.7}$, 0.5 ml of the $10^{-0.3}$ dilution were added into 2.0 ml. Repeat using the $10^{-1.0}$ dilution.

The appropriate volume from the first two tubes was removed to result in 2 ml final volume. These two were used to test neutralization of BNT/Esc.

A tertiary 10 fold dilution, $10^{-2.7}$, was made with 400 µl from the $10^{-1.7}$ dilution, adding it to 3.6 ml to give 4 ml.

The quaternary two fold dilutions were made by taking 2 ml of $10^{-2.7}$ dilution and serially diluting it two fold, and five times to conclude with a $10^{-4.2}$ dilution. This gave a range from 22.4 ug 7F8 to 700 ng 7F8 per tube.

As a positive control for BNT/F, 12.5 ul of pooled mouse anti-BNT/F sera, from the 27 Oct. 1994 bleed was diluted in 1.983 ml of PBS, to yield 2.0 ml. The end result is a 1:200 dilution.

As a negative control for BNT/F, 12.5 ul of pooled normal mouse sera was diluted in 1.983 ml of PBS, to yield 2.0 ml. The end result is a 1:200 dilution.

Preparation of BNT/Esc: 20 mice received 5 mLD50. Therefore required 3.0 ml of 50 mLD50 per ml (125 mLD50 total).

Preparation of BNT/F: 32 mice received 5 mLD50. Therefore required 5 ml of 50 mLD50 per ml (250 mLD50 total).

Neutralization of BNT/F

Half a ml of the diluted BNT/F stock or BNT/Esc stock was added, as appropriate, (25 mLD50s) to each of the appropriate 2.0 ml of diluted 7F8.G2.H3, or serum dilutions or negative controls resulting in a final volume of 2.5 ml which will contain 5 LDSOs per 0.5 ml. All the serum/BNT/$E_{SC}$ or serum/BNT/F preparations were incubated at 25° C. for 1 hour. Four mice were injected per preparation with 0.5 ml, IP.

Stoichiometry of 7F8.G2.H3 against BNT/F. Two fold dilutions.

| dil. | Day Ab/tube | BNT | 1 S/T | 2 S/T | 3 S/T | 6 S/T | 29 S/T |
|---|---|---|---|---|---|---|---|
| $10^{-2.7}$ | 22.4 ug | F | 4/4 | 4/4 | 4/4 | 4/4 | 4/4 |
| $10^{-3.0}$ | 11.2 ug | F | 4/4 | 4/4 | 4/4 | 4/4 | 4/4 |
| $10^{-3.3}$ | 5.6 ug | F | 4/4 | 4/4 | 4/4 | 4/4 | 4/4 |
| $10^{-3.6}$ | 2.8 ug | F | 4/4 | 4/4 | 4/4 | 2/4 | 2/4 |
| $10^{-3.9}$ | 1.4 ug | F | 4/4 | 2/4 | 1/4 | 1/4 | 1/4 |
| $10^{-4.2}$ | 700 ng | F | 3/4 | 0/4 | | | |
| | 1:200 MAF | F | 4/4 | 4/4 | 4/4 | 4/4 | 4/4 |
| | 1:200 NMS | F | 1/4 | 1/4 | 1/4 | 1/4 | 1/4 |
| Stoichiometry of 7F8.G2.H3 against BNT/F. | | | | | | | |
| $10^{-0.3}$ | 5.60 mg | Esc | 2/4 | 2/4 | 2/4 | 2/4 | 2/4 |
| $10^{-1.0}$ | 1.12 mg | Esc | 0/4 | | | | |
| $10^{-1.7}$ | 224 ug | Esc | 1/4 | 1/4 | 1/4 | 1/4 | 1/4 |
| | 1:200 MAF | Esc | 4/4 | 4/4 | 4/4 | 4/4 | 4/4 |
| | 1:200 NMS | Esc | 0/4 | | | | |

Protein Immunoblots Following SDS PAGE or Native PAGE

BNT/F and BNT/$E_{SC}$ stock solutions were mixed with equal volumes of 2× SDS sample buffer and heated to 95°

Figure 2:
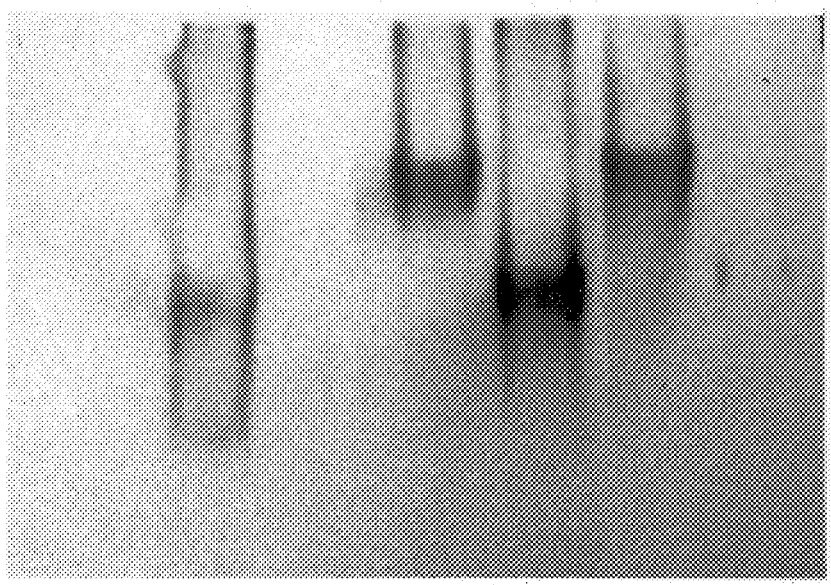
FIG. 2 shows a native blot of mAb 7F8.G2.H3 against botulinum neurtotoxins E and F.

C. for five minutes prior to use (FIG. 1). Alternatively both stock solutions were mixed with equal volumes of 2× sample buffer without SDS and kept at −20° C. until needed (FIG. 2). Reducing agents were not used. Samples volumes were adjusted to apply 1.5 µg of protein in 2 to 5 ul volumes. SDS PAGE was conducted on 10% total acrylamide gels, with 3% cross-linking, while Native PAGE was conducted on 7.5% acrylamide gels, with 3% cross-linking. SDS-PAGE was run at 20 mA and Native PAGE was run at 10 mA, with cooling. Proteins were transferred to nitrocellulose for blotting using Tris-Glycine buffers with 20% methanol (for SDS-PAGE) or without methanol (for Native PAGE). Nitrocellulose was blocked with 5% skim milk. All primary antibodies and the secondary HRP-conjugated antibody were used at 1:2000 dilutions. The luminol-based assay system of Kirkegaard & Perry was employed to develop the blots.

Results from SDS-PAGE are shown in FIG. 1. Monoclonal antibody 7F8.G2.H3 does not detect either BNT/E$_{SC}$ nor BNT/F when the BNT is denatured. The mouse sera from BNT/F immunized mice does recognize denatured BNT/F as well as BNT/E$_{SC}$. The mice had been previously immunized with BNT/E$_{SC}$. However mice that had been immunized only with BNT/E$_{SC}$ had sera that recognized denatured BNT/E, but not denatured BNT/F.

Results from Native PAGE are shown in FIG. 2. Monoclonal antibody 7F8.G2.H3 does not detect native BNT/E$_{SC}$, but does detect native BNT/F. The mouse sera from BNT/F immunized mice still recognize BNT/F as well as BNT/E$_{SC}$. Mice that had been immunized with BNT/E$_{SC}$ have sera that recognize BNT/E, but also recognize native BNT/F.

In Vivo Neutralization Assay

Mice received an intravenous (IV) injection of 50 µl of the stock ascites antibody (7F8.G2.H3) in PBS (280 ug mouse antibody per mouse) or PBS. One hour later they were challenged with 5 IP mLD50 (280 pg/mouse). Results are expressed as survivors/total.

| | In vivo neutralization assay: | | | | | |
|---|---|---|---|---|---|---|
| Group | Day 1 S/T | 2 S/T | 3 S/T | 6 S/T | 10 S/T | 21 S/T |
| 7F8 Ascites | 4/4 | 4/4 | 4/4 | 4/4 | 4/4 | 4/4 |
| PBS | 1/4 | 0/4 | | | | |

Second In Vivo Neutralization Assay

Mice received an intravenous (IV) injection of 50 µl of the stock ascites antibody (7F8.G2.H3) in PBS (280 ug mouse antibody per mouse) or PBS. One hour later they were challenged with varying IP mLD$_{50}$ doses. Results are expressed as survivors total.

| | | DATA is expresses as Survivors/Total | | | | | |
|---|---|---|---|---|---|---|---|
| Group IV | | BNT/F IP mLD$_{50}$ | 1d | 2d | 3d | 5d | 21d |
| Control 1 | PBS | 5 | 2/3 | 2/31 | 1/3 | 1/3 | 1/3 |
| Control 2 | PBS | 50 | 0/3 | | | | |
| Test 1 | 7F8 | 5 | 4/4 | 4/4 | 4/4 | 4/4 | 4/4 |
| Test 2 | 7F8 | 50 | 4/4 | 4/4 | 4/4 | 4/4 | 4/4 |
| Test 3 | 7F8 | 500 | 4/4 | 1/4 | 1/4 | 1/4 | 1/4 |
| Test 4 | 7F8 | 5000 | 1/4 | 1/4 | 1/4 | 1/4 | 1/4 |
| Test 5 | 7F8 | 50000 | 0/4 | | | | |

What is claimed is:

1. A neutralizing monoclonal antibody specific to the active form of botulinum neurotoxin serotype F, BNT/F.

2. A monoclonal antibody according to claim 1 which is produced by a hybridoma between a mouse myeloma cell and a spleen cell of a mouse immunized with BNT/F.

3. A monoclonal antibody according to claim 2 wherein said hybridoma is F197/7F8.G2.H3 having ATCC designation HB-12102.

4. A monoclonal antibody according to claim 3 wherein said monoclonal antibody is 7F8.G2.H3.

5. A hybridoma having ATCC designation HB12102 which produces a monoclonal antibody according to claim 1 and progeny of said hybridoma.

6. A protein comprising the antigen binding domain of the monoclonal antibody of claim 4.

7. A neutralizing monoclonal antibody according to claim 1 produced by the method comprising the step of immunizing with native botulinum neurotoxin serotype F.

* * * * *